(12) United States Patent
Davey

(10) Patent No.: US 6,432,091 B1
(45) Date of Patent: Aug. 13, 2002

(54) VALVED OVER-THE-WIRE CATHETER

(75) Inventor: Christopher T. Davey, Boston, MA (US)

(73) Assignee: Sci Med Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/465,153

(22) Filed: Dec. 16, 1999

(51) Int. Cl.⁷ ................................................. A61M 5/31
(52) U.S. Cl. ...................................... 604/246; 604/249
(58) Field of Search .................................. 604/278, 537, 604/526, 246, 247, 122, 99.02–99.04, 264, 523, 249, 256

(56) References Cited

U.S. PATENT DOCUMENTS

| | | |
|---|---|---|
| 4,023,559 A | 5/1977 | Gaskell |
| 4,549,879 A | 10/1985 | Groshong et al. |
| 4,701,166 A | 10/1987 | Groshong et al. |
| 5,030,210 A | 7/1991 | Alchas |
| 5,049,138 A | 9/1991 | Chevaliet |
| 5,120,816 A | 6/1992 | Gould et al. |
| 5,147,318 A | 9/1992 | Hohn |
| 5,171,222 A | 12/1992 | Euteneuer et al. |
| 5,224,938 A | 7/1993 | Fenton, Jr. |
| 5,250,034 A | 10/1993 | Appling et al. |
| 5,259,839 A | 11/1993 | Burns |
| 5,261,885 A | 11/1993 | Lui |
| 5,324,259 A | 6/1994 | Taylor et al. |
| 5,348,537 A | 9/1994 | Wiesner et al. |
| 5,522,807 A | 6/1996 | Luther |
| 5,807,349 A | 9/1998 | Person et al. |
| 5,919,162 A | 7/1999 | Burns |
| 5,928,203 A | 7/1999 | Davey et al. |

Primary Examiner—Brian L. Casler
Assistant Examiner—Kevin C. Sirmons
(74) Attorney, Agent, or Firm—Hoffmann & Baron LLP

(57) ABSTRACT

An over-the-wire catheter with a sealable distal end is provided. The distal end is capable for forming a fluid tight seal by action of a hydrophilicly expandable valve. The valve is also a lubricous composition to provide for a guidewire that slidably moves through the distal end of the catheter.

23 Claims, 4 Drawing Sheets

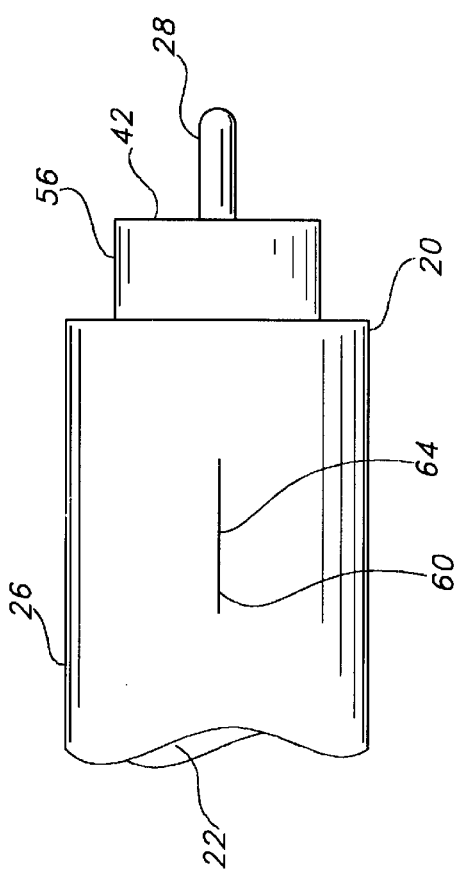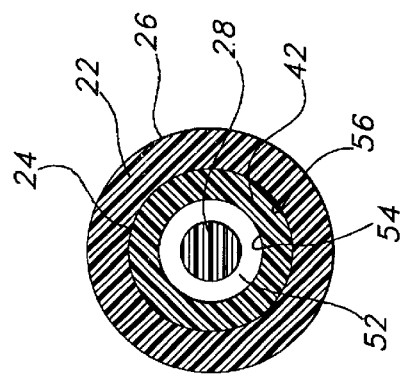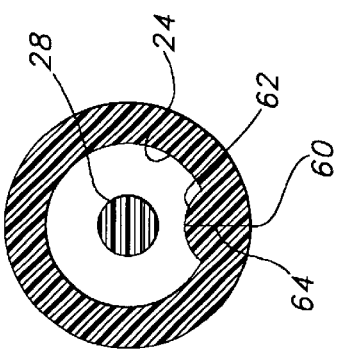

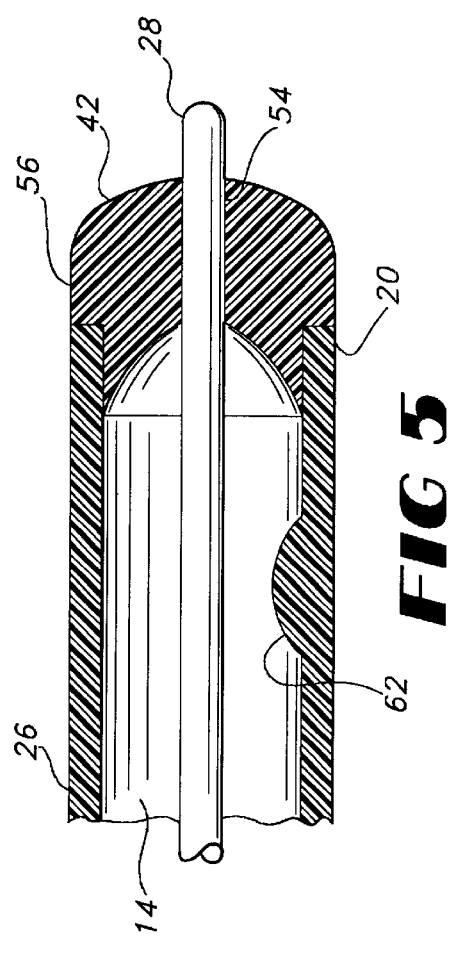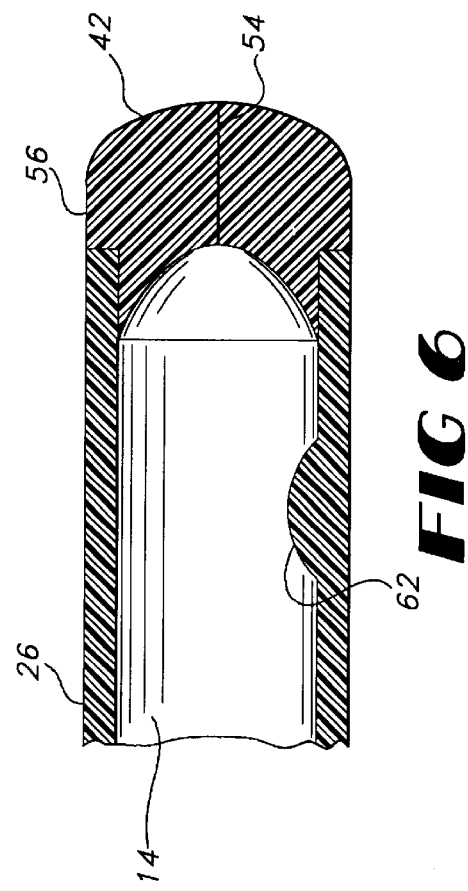

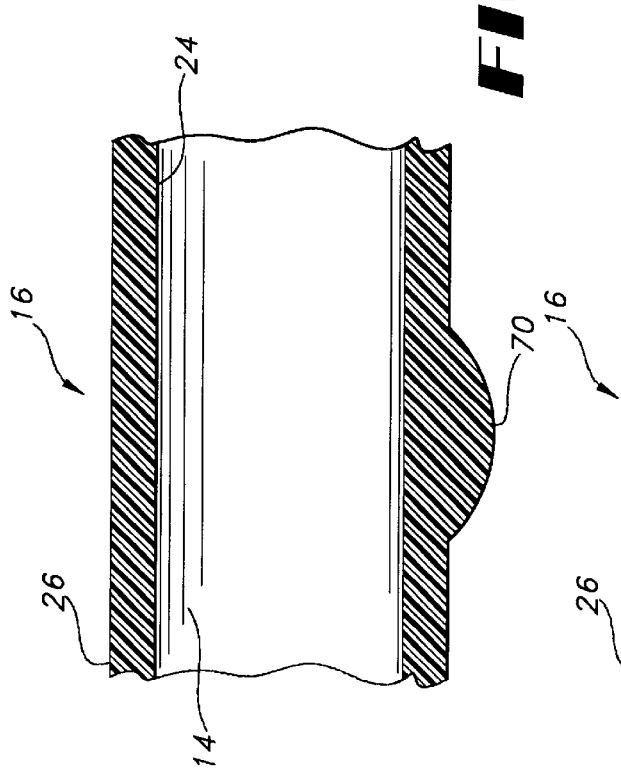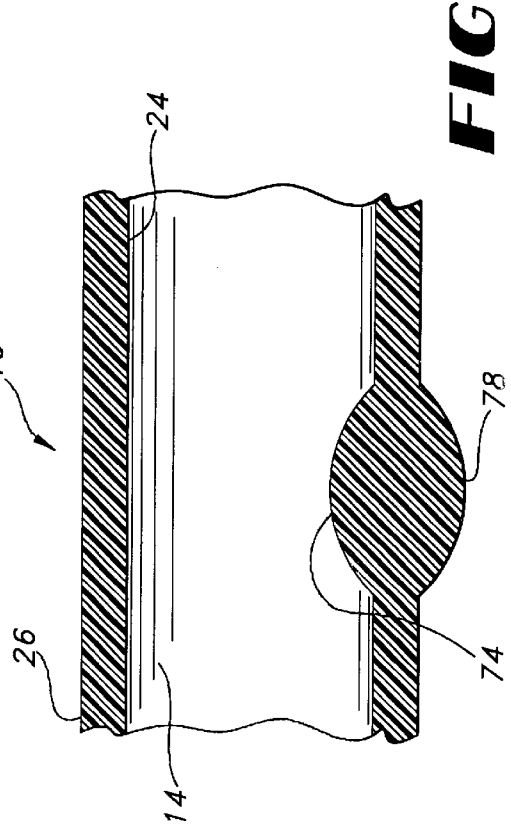

VALVED OVER-THE-WIRE CATHETER

FIELD OF THE INVENTION

The present invention relates to a valved over-the-wire catheter. More particularly, the present invention relates a valved over-the-wire catheter with a hydrophilicly sealable distal tip capable of passing a guidewire.

BACKGROUND OF THE INVENTION

Catheters are well known for use with the human body as part of diagnostic or treatment procedures. Such devices are typically introduced through body lumens such as blood vessels and are advanced to an area designated for diagnosis or treatment. For example, a central venous catheter is often used to provide intravenous access into a portion of a person's blood system. The central venous catheter may then be used to inject or withdraw fluids into or from a patient's blood stream. The injection of a medication and the withdrawal of a blood sample are common uses of a central venous catheter.

One type of catheter used for such intravenous access has an open distal, or implantable, end. The open distal end allows for the injection or withdrawal of fluids between the lumen of the catheter and the body lumen. The proximal, or non-implantable, end of the catheter is connected to a syringe or other suitable device for injecting or withdrawing fluid to or from the lumen of the catheter.

Another type of catheter for such intravenous access has a closed distal end. A closed-end catheter typically has infusion or aspiration valves at the distal end for injecting or withdrawing fluids. Infusion or aspiration valves are generally slits or slots in the distal tip of the catheter. Infusion is accomplished by imparting a positive pressure at an internal lumen of the catheter (i.e., a greater pressure than the vascular pressure) to inject a fluid from the catheter into the body lumen. Aspiration is accomplished by applying negative pressure (i.e., a pressure less than the vascular pressure) within the catheter lumen to draw vascular fluid into the catheter lumen. The infusion/aspiration valves typically open with moderate or low pressure or mechanical force and close upon the removal of that pressure or force. The proximal end is connected to a syringe or other suitable device for injecting or withdrawing fluids.

A closed-distal-end catheter is configured to minimize contact between the interior lumen of the catheter and the environment outside of the catheter, i.e., a body lumen. Such contact is minimized because the distal tip is closed and the infusion and aspiration valves can be closed to isolate the interior lumen of the catheter from its outside environment. The interior lumen of an open-distal-end catheter cannot be so isolated from its outside environment, thereby increasing the potential for thrombosis, for instance, thrombosis formation at the open distal tip.

A closed-distal-end catheter, however, cannot be easily exchanged over a guidewire. A guidewire is useful in certain procedures. For instance, if a catheter is to be advanced to a body site through a tortuous vascular path or through small vascular lumens, then the use of a guidewire may facilitate the placement of the catheter. In such a case, the guidewire may be advanced to a desired body site, and the open-distal-ended catheter may be then slidingly engaged along the guidewire to the desired body site. When the distal tip of the catheter is at the desired site, the guidewire is removed while keeping the catheter positioned at the desired site. Moreover, if an indwelling catheter has to be exchanged with a replacement catheter, then a guidewire may be used to remove the indwelling catheter and to position the replacement catheter at the same site. After the exchange, the guidewire is removed.

To use a guidewire with a closed-distal-end catheter, the guidewire, if possible, is passed through the infusion or aspiration valves at the distal end of the catheter. The passing of guidewires through these valves, however, often runs the risk of damaging the valve integrity. Such damage may prevent the valve from providing a fluid tight seal between the vascular lumen and the interior lumen of the catheter. Moreover, it is often difficult to pass a guidewire through a valve of an indwelling catheter because the valves are typically located in the wall of the catheter, thereby making passage of a guidewire difficult.

Accordingly, it is desirable to provide a catheter capable of passing over a guidewire without the disadvantages as described above. More desirably, there is a need for a valved catheter with the ability to navigate through small vascular lumens typical of some treatment areas while also having the capability of being slidably engaged and disengaged over a guidewire without the disadvantages of typical closed-ended catheters.

SUMMARY OF THE INVENTION

The present invention is directed to a catheter in the form of a sealable means for sealing the distal end of the catheter after passing a guidewire. The sealable means is a valve capable of hydrophilic expansion upon contact with an aqueous fluid. Initially, the distal end is open as the catheter is implanted into a vascular lumen. Such an open end allows for easy passage of a guidewire through the distal end. Upon contact with an aqueous fluid the valve closes to seal the distal end of the catheter with the guidewire thereat to form a distal tip with a smooth, contoured profile more typical of a closed-end catheter to reduce the potential of thrombosis.

The valve at the distal end of the catheter incorporates a lubricous composition to facilitate longitudinal movement of a guidewire therethrough. The lubricous composition is pliable so that the valve is adaptable for infusion without effecting the integrity of the valve surface for maintaining a fluid tight seal.

BRIEF DESCRIPTION OF THE DRAWINGS

FIG. 2 depicts a cross-sectional view of the catheter of FIG. 1 taken along the 2—2 axis.

FIG. 3 depicts a second cross-sectional view of the catheter of FIG. 1 taken along the 3—3 axis.

FIG. 4 depicts a partial elevational view of the catheter of FIG. 1 showing an aspiration valve at the distal portion thereat.

FIG. 5 depicts a partial longitudinal cross-sectional view of the distal tip of the catheter of FIG. 1 having a valve in a closed position to form a fluid tight seal about a guidewire.

FIG. 6 depicts a partial longitudinal cross-sectional view of the distal tip of the catheter of FIG. 1 having a valve in a closed position to form a fluid tight seal at the distal end of the catheter.

FIG. 7 depicts a partial elevational view of the catheter of FIG. 1 showing an infusion valve at the distal portion thereat.

FIG. 8 depicts a partial elevational view of the catheter of FIG. 1 showing an aspiration/infusion valve at the distal portion thereat.

DETAILED DESCRIPTION OF THE INVENTION

Figure 1:
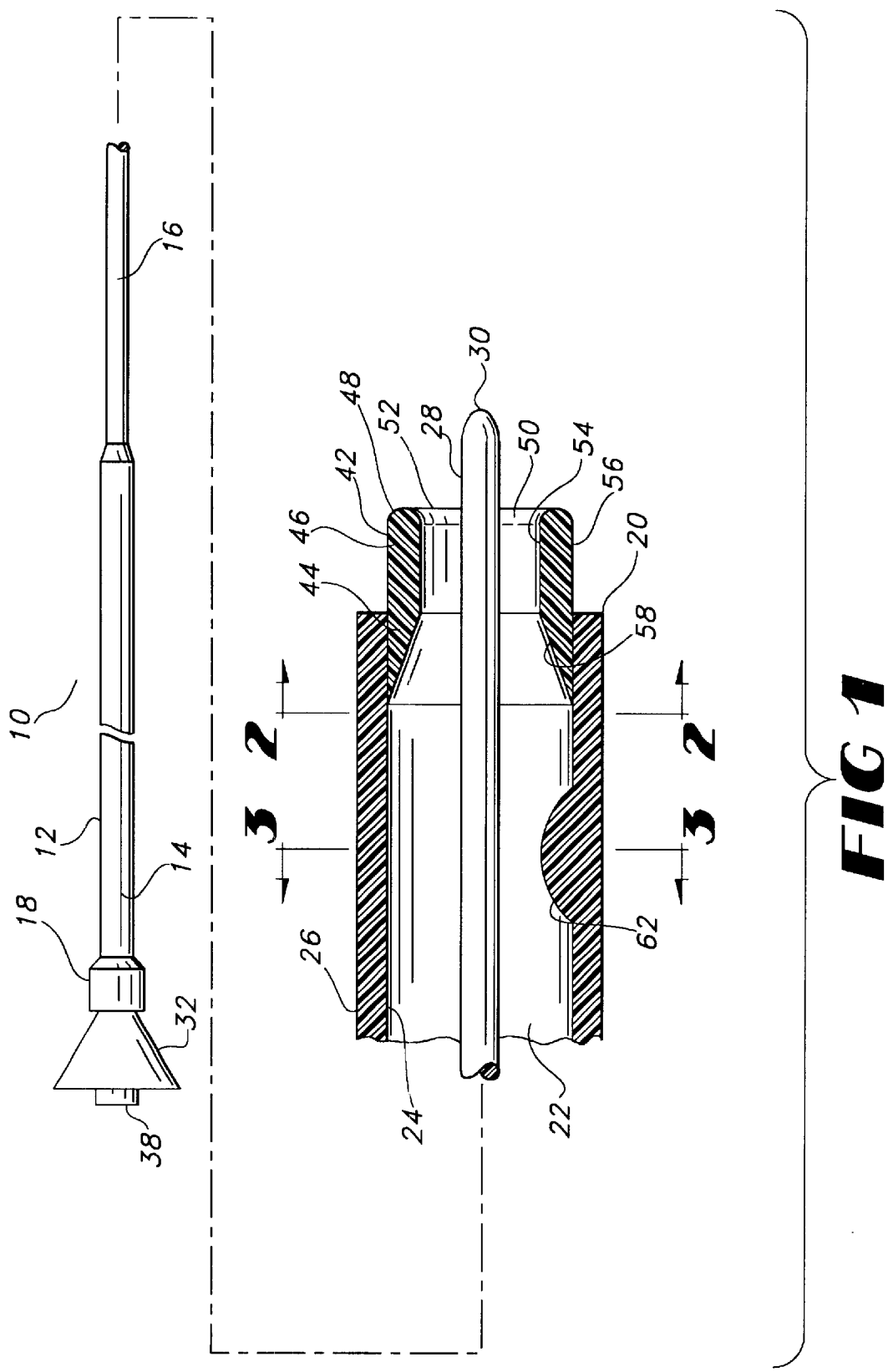
FIG. 1 depicts an elevational view with partial longitudinal cross section of a single lumen over-the wire catheter of the present invention.

The present invention provides an intravascular percutaneous catheter system including a catheter with a hydrophilicly expandable valve or sealing mechanism at the distal end of the catheter. The sealing mechanism expands upon contact with an aqueous fluid to seal the distal end of the catheter. The sealing mechanism can also accommodate a guidewire which slidably extends through the sealing mechanism at the distal end of the catheter.

FIG. 1 is an elevational view of catheter 10 of the present invention. Catheter 10 includes an elongate catheter shaft 12 including a proximal portion 14 and a narrow distal portion 16. Catheter 10 includes a single lumen 22 defined by inner surface 24 and an opposed outer surface 26 of catheter shaft 12. A guidewire 28 is positionable through lumen 22 to extend out through a distal end 20 of catheter shaft 12. Catheter 10 further includes a fitting 32, for example, a standard luer lock, on a proximal end 18 of catheter shaft 12 which is adapted to infuse a liquid into the lumen 22 or to aspire a liquid from the lumen 22. Fitting 32 has a port 38 connected to an infusion/aspiration device (not shown). The infusion/aspiration device may be a syringe or other suitable device for injecting or withdrawing fluid from the lumen 22.

Guidewire 28 may be any guidewire as is known in the art. Guidewire is typically an elongated, relatively rigid cylindrical member. Guidewire 28 may be constructed of any material, but is preferably constructed of metal, such as stainless steel.

Moreover, guidewire 28 may have a constant stiffness or flexibility along the entire length thereof, or may have portions of varying stiffness and flexibility, such as an area of increased flexibility at guidewire tip 30. Guidewire 28 may further include a coating along a portion or the entire length thereof, such as a lubricious or frictionless coating material. Guidewire 28 may further be provided with a radio opaque portion, for example in the form of a radio opaque coating on a portion of the guidewire, or by constructing a portion of the guidewire out of a radio opaque material.

Catheter 10 may be any type of catheter known in the art for use in conjunction with a guidewire, and is generally flexible along the length thereof. Catheter 10 is not limited to a single lumen configuration, for instance single lumen 22, but may be configured with multiple lumens. Furthermore, catheter shaft 12 may be constructed of any biocompatible material known in the art. Desirably, catheter shaft 12 is constructed of polymeric material, more desirably a polymeric material selected from polyethylene, polypropylene, polystyrene, polyester, polyurethane, polyamide, peboxes, and the like, and mixtures and combinations thereof.

The present invention provides a valve 42 secured to the lumen 22 at the distal end 20 of catheter shaft 12. As shown in FIG. 1, valve 42 is a tubular member formed of a deformable biocompatible elastomer. Valve 42 includes a proximal extent 44 dimensioned for insertion into the distal end 20 of catheter shaft 12. Valve 42 includes an opposed distal extent 46 which extends outwardly of distal end 20. The end wall 48 of distal extent 46 may be rounded to facilitate smooth movement of catheter shaft 12 within a body vessel. Valve 42 defines a valve lumen 50 which is generally co-linear with catheter lumen 22. Valve lumen 50 is defined by an inner surface 54 of valve 42. Valve 42 is adapted to receive guidewire 28 through valve lumen 50. The distal extent 46 of valve 42 defines a valve aperture 52. As depicted in FIG. 1, the valve 42 is in an open position allowing for easy sliding longitudinal movement of guidewire 28 through valve aperture 52. Such movement is facilitated through valve 42 by tapered walls 58 thereof. The valve 42 is capable of achieving a closed position to establish a fluid tight seal between lumen 22 and the body fluid. As described further herein, the valve 42 is also adapted to allow guidewire 28 to slidably move while the valve 42 is in the closed position.

Desirably, valve 42 contains a lubricous composition to facilitate placement of catheter 10 within the body and movement of the guidewire 28. More desirably, valve 42 is a hydrophilic polymer capable of hydration upon contact with an aqueous fluid and further capable of dehydration upon the absence of an aqueous fluid. As used herein, the term "aqueous" and its variants refer to a fluid medium, including body fluids, that contain water. Useful hydrophillic polymers include hydrophilic polyether polyurethanes, which in the presence of aqueous fluids convert to hydrogels. The water content of these hydrophilic polymers can be varied from 1% to 99%, depending upon the desired chemical, physical and release properties. At the composition absorbs water, the composition expands or swells. The degree of swelling can be controlled to a desired magnitude and desired direction at different water contents. By controlling the crosslinking of the polymer structure, the polymer can exhibit uni-directional swelling.

The hydrophilic polymers can be used in conventional processing techniques including extrusion, co-extrusion, blow-molding, injection molding and dipping. Useful processing include co-extrusion by which the lubricous composition may be physically secured to the catheter shaft 12. For example, a portion of outer surface 56 of valve 42 is secured to a portion of inner lumen surface 24 at the distal end 20 of catheter shaft 12. Such hydrophilic polyurethanes are substantially non-covalently crosslinked reaction products of poly(oxyalkylene) glycols and organic diisocynnates and are available from Tyndale Plains-Hunter, Ltd. of Princeton, N.J.

FIG. 2 is a cross sectional view of the distal end 20 of catheter shaft 12 taken along the 2—2 axis. Outer surface 56 of valve 42 is secured to the interior portion of lumen 22. Valve 42 is in a quiescent state allowing passage of guidewire 28 therethrough. As used herein, the term "quiescent" and its variants refer to a state in which the hydrophillic composition has not yet substantially expanded due to the absorption of an aqueous fluid. As depicted in FIG. 2, inner surface 54 of valve 42 in its quiescent state does not abuttingly engage guidewire 28. The present invention, however, is not limited to such non-abutting engagement. For example, inner surface 54 may engage a portion or a substantial portion of guidewire 28 in the quiescent state. Guidewire 28 may slidably engage inner surface 54 when the lubricous composition is in its quiescent state.

FIG. 5 depicts a cross sectional view of the distal end 20 of catheter shaft 12 wherein valve 42 is in an expanded or a closed position. Upon absorption of an aqueous fluid inner surface 54 hydrophilicly expands to engage guidewire 28. Desirably, inner surface 54 engages guidewire 28 to form a fluid tight seal thereat. Outer surface 56 of valve 42 also hydrophilicly expands upon the absorption of an aqueous fluid. Desirably, the degree of expansion or swelling in the expanded state is such that outer surface 56 of valve 42 is substantially circumjacent to the outer surface 26 of lumen 22. Moreover, it is desirable that the outer surface 56 of valve 42 in its expanded state should not circumferentially extent beyond the outer surface 26 of lumen 22. Furthermore, it is desirable that the outer surface 56 of valve 42 in its expanded shape forms a smooth contoured shape.

The lubricous nature of valve 42 permits longitudinal movement of the guidewire 28 through valve 42 even when the valve 42 is in a closed position. Positive pressure, as supplied by an infusion fluid, may also be used to reduce friction between the guidewire 28 and the inner surface 54 of valve 42, thereby allowing more easily movement of the catheter 10 over the guidewire 28.

Furthermore, as depicted in FIG. 6, valve 42 can form a fluid tight seal without the presence of guidewire 28. Inner surface 54 of valve 42 can hydrophilicly expand to form a fluid tight seal at the distal end 20 of catheter shaft 12.

The distal end of the catheter shaft 12 shows an aspiration valve 60, which is useful with the present invention. As depicted in FIGS. 3 and 4, aspiration valve 60 further includes protuberance 62 at the inner lumen surface 24 of lumen 22 and slit 64 which extends throughout protuberance 62 and lumen 22 to provide fluid communication between lumen 22 and a body lumen. Upon application of a negative pressure slit 64 opens to allow aspiration. In a nonaspirational mode slit 64 is closed to form a fluid tight seal. Protuberance 62 is configured to allow fluid communication only upon aspiration. Upon infusion of lumen 22, the protuberance 62 is configured to form a fluid tight seal at slit 64 and prevent infusion thereat.

Catheter 10 of the present invention may incorporate other types of infusion valves beyond that which is shown herein. For, example U.S. Pat. No. 5,928,203, which is incorporated by reference herein, discloses infusion, aspiration and infusion/aspiration valves useful with the present invention. Such valves may include a slitted protuberance which can be located at various positions along the catheter. For example, the present invention may employ an interior protuberance, as depicted in FIG. 1, which is particularly useful for aspiration. As shown in FIG. 7, the distal end 16 of catheter 10 may include an exterior protuberance 70 on the exterior surface 26 of lumen 22. Such an exterior protuberance is useful as an infusion valve. Further, as shown in FIG. 8, opposed protuberances 74 and 78 respectively on the inner surface 24 and outer surface 26 of lumen 22 at the distal portion 16 are useful as an infusion/aspiration valve. The height of the protuberance may be varied to control the pressure at which infusion or aspiration is desired.

The present invention is not limited to the use of slitted protuberances as aspiration and infusion valves. Other wellknown aspiration and infusion valves may suitably be used with the present invention. For example, a radial slit that is longitudinal or at an angle to the longitudinal axis of the lumen may be used for either aspiration or infusion. Unidirectional valves, for instance infusion-only or aspirationonly valves, may also be formed by altering the geometry of the lumen proximal or by altering the geometry of the slit. One means for providing a unidirectional valve by altering the geometry of the lumen is to form a slit in a non-convex surface of the lumen. Such non-convex surfaces may be more suitable for aspiration as compared to a slit in a convex surface. Non-radial slits, such as centrifugal or centripetal slits, may also be suitable configured for unidirectional valves. A slit may for a slot-shaped valve or other suitable shape, for instance an arced shaped slit. Examples of these various configurations are known, see for example U.S. Pat. Nos. 5,224,938; 5,250,034; 5,261,885; 5,522,807 and 5,807, 349.

Moreover, valve 42 is desirably configured to allow for infusion. The lubricous composition of valve 42 is sufficiently pliable so that inner surface 54 of valve 42 moves away from guidewire 28 upon application of a positive pressure within lumen 22. Furthermore, the lubricous composition is sufficiently resilient to return to its shape in a closed position to form a fluid tight seal upon the removal of the infusion pressure.

While the present invention has been described in terms of a preferred embodiment and use, those skilled in the art will readily recognize that various modifications can be made without departing from the scope of the present invention.

What is claimed is:

1. A intravascular percutaneous device comprising:
   an elongate member having a tubular wall defined by an inner surface, an opposed outer surface and a passageway longitudinally therethrough, and having a distal end implantable into a vascular lumen; and
   a valve member formed of a lubricous composition at said distal end of said elongate member, said valve member defining a first open position in a quiescent state to allow fluid communication through said distal end and a second closed position in an expanded state to prevent fluid communication through said distal end;
   wherein said lubricous composition hydrophilicly expands upon contact with an aqueous fluid to move said valve member from said quiescent state to said expanded state.

2. The device of claim 1 wherein said device is a catheter.

3. The device of claim 1 further including a slit extending through a distal portion of said tubular wall of said elongate member, said slit being operable in response to pressure within said elongate member to open to allow fluid communication through said tubular wall and close to prevent fluid communication through said tubular wall.

4. The device of claim 1 further including an aspiration slit extending through a distal portion of said tubular wall of said elongate member, wherein said aspiration slit is in a closed position to prevent fluid communication through said tubular wall upon application of an positive pressure within said elongate member, said positive pressure being greater than or equal to a vascular pressure of said vascular lumen, and further wherein said aspiration slit is in an open position upon application of negative pressure within said elongate member to allow fluid communication through said tubular wall, said negative pressure being less than the vascular pressure of said vascular lumen.

5. The device of claim 4 further including an internal protuberance disposed on said inner surface of said tubular wall at said distal portion of said elongate member, wherein said aspiration slit extends through said tubular wall and said internal protuberance to effect an amount of negative pressure for allowing fluid communication.

6. The device of claim 1 further including an infusion slit extending through at a distal portion of said tubular wall of said elongate member, wherein said infusion slit is in a closed position to prevent fluid communication through said tubular wall upon application of an negative pressure within said elongate member, said negative pressure being lesser than or equal to a vascular pressure of said vascular lumen, and further wherein said infusion slit is in an open position upon application of positive pressure within said elongate member to allow fluid communication through said tubular wall, said positive pressure being greater than the vascular pressure of said vascular lumen.

7. The device of claim 6 further including an external protuberance disposed on said outer surface of said tubular wall at said distal portion of said elongate member, wherein said infusion slit extends through said tubular wall and said external protuberance to effect an amount of positive pressure for allowing fluid communication.

8. The device of claim 1 wherein upon application of a fluid pressure within said elongate member, said lubricious composition remains in said expanded state to prevent fluid communication through said distal end, said fluid pressure being greater than or equal to a vascular pressure of said vascular lumen.

9. The device of claim 1 wherein upon application of a fluid pressure within said elongate member said lubricious composition is capable of movement from said second closed position to a third position to allow fluid communication through said distal end, said fluid pressure being greater than a vascular pressure of said vascular lumen.

10. The device of claim 9 wherein said lubricous composition is pliable to allow infusion.

11. The device of claim 9 wherein said lubricous composition is resilient to return to said second closed position upon the removal of the fluid pressure.

12. The device of claim 9 further including a guidewire extending longitudinally throughout said passageway, wherein said guidewire is capable of passing through said distal end when said lubricious composition is in said third position.

13. The device of claim 1 further including a guidewire extending longitudinally throughout said passageway, wherein said guidewire is capable of passing through said distal end when said lubricious composition is in said quiescent state.

14. The device of claim 13 wherein said lubricous composition in said expanded state forms a seal at a portion of said guidewire to prevent fluid communication through said distal end.

15. An over-the-wire catheter comprising:
    an elongate member having a tubular wall defined by an inner surface, an opposed outer surface and a passageway longitudinally therethrough, and having a distal end implantable into a vascular lumen;
    a guide wire longitudinally disposed throughout a portion of said passageway and extending through said distal end; and
    a valve member formed of a lubricous composition disposed at said distal end of said elongate member, said valve member defining a first open position in a quiescent state to allow fluid communication through said distal end and a second closed position in an expanded state to seal said guidewire to prevent fluid communication through said distal end;
    wherein said lubricous composition hydrophilicly expands upon contact with an aqueous fluid to move said valve member from said quiescent state to said expanded state.

16. The catheter of claim 14 wherein said guidewire slidably engages said lubricous composition when said lubricous composition is in said expanded state to allow movement of said catheter over said guidewire.

17. The catheter of claim 15 wherein upon application of a fluid pressure said lubricous composition is capable of movement from said second closed position to a third position to allow fluid communication through said distal end.

18. The catheter of claim 17 wherein said lubricous composition is pliable to allow infusion.

19. The catheter of claim 17 wherein said lubricous composition is resilient to return to said second closed position upon the removal of the fluid pressure.

20. The catheter of claim 15 further including a slit extending through a distal portion of said tubular wall of said elongate member, said slit being operable in response to pressure within said elongate member to open to allow fluid communication through said tubular wall and close to prevent fluid communication through said tubular wall.

21. The catheter of claim 15 further including an aspiration slit extending through a distal portion of said tubular wall of said elongate member, wherein said aspiration slit is in a closed position to prevent fluid communication through said tubular wall upon application of an positive pressure within said elongate member, said positive pressure being greater than or equal to a vascular pressure of said vascular lumen, and further wherein said aspiration slit is in an open position upon application of negative pressure within said elongate member to allow fluid communication through said tubular wall, said negative pressure being less than the vascular pressure of said vascular lumen.

22. The catheter of claim 15 further including an infusion slit extending through a distal portion of said tubular wall of said elongate member, wherein said infusion slit is in a closed position to prevent fluid communication through said tubular wall upon application of an negative pressure within said elongate member, said negative pressure being lesser than or equal to a vascular pressure of said vascular lumen, and further wherein said infusion slit is in an open position upon application of positive pressure within said elongate member to allow fluid communication through said tubular wall, said positive pressure being greater than the vascular pressure of said vascular lumen.

23. An over-the-wire catheter with aspiration and infusion valves comprising:
    an elongate member having a tubular wall defined by an inner surface, an opposed outer surface and a passageway longitudinally therethrough, and having a distal end implantable into a vascular lumen;
    a guide wire longitudinally disposed throughout a portion of said passageway and extending through said distal end;
    an aspiration valve at a distal portion of said elongate member having an aspiration slit extending through said tubular wall, wherein said aspiration slit is in a closed position to prevent fluid communication through said tubular wall upon application of an positive pressure within said elongate member, said positive pressure being greater than or equal to a vascular pressure of said vascular lumen, and further wherein said aspiration slit is in an open position upon application of negative pressure within said elongate member to allow fluid communication through said tubular wall, said negative pressure being less than the vascular pressure of said vascular lumen;
    an infusion valve at a distal portion of said elongate member having an infusion slit extending through said tubular wall, wherein said infusion slit is in a closed position to prevent fluid communication through said tubular wall upon application of an negative pressure within said elongate member, said negative pressure being lesser than or equal to a vascular pressure of said vascular lumen, and further wherein said infusion slit is in an open position upon application of positive pressure within said elongate member to allow fluid communication through said tubular wall, said positive pressure being greater than the vascular pressure of said vascular lumen; and a valve member formed of a lubricous composition disposed at said distal end of said elongate member, said valve member defining a first open position in a quiescent state to allow fluid communication through said distal end and a second closed position in an expanded state to seal said guidewire to prevent fluid communication through said distal end;

wherein said lubricous composition hydrophilicly expands upon contact with an aqueous fluid to move said valve member from said quiescent state to said expanded state.

* * * * *